(12) United States Patent
Santini et al.

(10) Patent No.: US 9,816,949 B2
(45) Date of Patent: Nov. 14, 2017

(54) METHOD OF ANALYSING GROUND COFFEE

(71) Applicants: Gruppo Cimbali S.p.A., Binasco (IT); Università degli Studi di Bergamo, Bergamo (IT)

(72) Inventors: Maurizio Santini, Bergamo (IT); Stefano Paleari, Bergamo (IT); Alberto Galimberti, Binasco (IT); Guido Quaratesi, Binasco (IT)

(73) Assignees: GRUPPO CIMBALI S.P.A., Binasco (IT); UNIVERSITÀ DEGLI STUDI DI BERGAMO, Bergamo (IT)

( * ) Notice: Subject to any disclaimer, the term of this patent is extended or adjusted under 35 U.S.C. 154(b) by 84 days.

(21) Appl. No.: 14/972,935

(22) Filed: Dec. 17, 2015

(65) Prior Publication Data
US 2016/0178539 A1    Jun. 23, 2016

(30) Foreign Application Priority Data
Dec. 18, 2014 (IT) .................. MI14A2179

(51) Int. Cl.
| | |
|---|---|
| G06K 9/00 | (2006.01) |
| G01N 23/04 | (2006.01) |
| G01N 33/02 | (2006.01) |
| G06T 5/20 | (2006.01) |
| G06T 7/00 | (2017.01) |

(Continued)

(52) U.S. Cl.
CPC ....... *G01N 23/046* (2013.01); *G01N 15/0227* (2013.01); *G01N 33/02* (2013.01); *G06T 5/20* (2013.01); *G06T 7/0004* (2013.01); *G06T 11/008* (2013.01); *G01N 2033/0091* (2013.01); *G06T 2207/10016* (2013.01); *G06T 2207/10081* (2013.01); *G06T 2207/20028* (2013.01);

(Continued)

(58) Field of Classification Search
None
See application file for complete search history.

(56) References Cited

U.S. PATENT DOCUMENTS

2014/0241590 A1    8/2014  Day, Jr. et al.

FOREIGN PATENT DOCUMENTS

| WO | 2009040249 A1 | 4/2009 |
| WO | 2012069359 A1 | 5/2012 |

OTHER PUBLICATIONS

Pittia et al., Paola, "Evaluation of microstructural properties of coffee beans by synchrotron X-ray microtomography: a methodological approach", Journal of Food Science, vol. 76 (2011), pp. 222-231.

(Continued)

*Primary Examiner* — Vikkram Bali
(74) *Attorney, Agent, or Firm* — Alan G. Towner, Esq.; Leech Tishman Fuscaldo & Lampl

(57) ABSTRACT

Method for analyzing the structure of a sample of ground coffee, and in particular for determining the grain size curve, by means of computed X-ray tomography, the method comprising: acquiring a plurality of two-dimensional radiographic images while the sample is in rotation, processing the plurality of two-dimensional radiographic images performing a tomographic reconstruction to generate a reconstructed image of volume, processing the reconstructed volume image to identify a plurality of coffee particles of the sample of ground coffee separated from one another and determining at least one dimensional magnitude for each particle of ground coffee of the plurality.

14 Claims, 8 Drawing Sheets

(51) Int. Cl.
    *G06T 11/00*     (2006.01)
    *G01N 15/02*     (2006.01)
    *G01N 33/00*     (2006.01)
(52) U.S. Cl.
    CPC ............... *G06T 2207/30128* (2013.01); *G06T 2207/30242* (2013.01)

(56) References Cited

OTHER PUBLICATIONS

Frisullo et al., P., "Coffea arabica beans microstructural changes induced by roasting: An X-ray microtomographic investigation", Journal of Food Engineering, vol. 108 (2012), Aug. 2011, pp. 232-237, Elsevier Ltd.
Santini et al., Maurizio, "X-ray computed microtomography for drop shape analysis and contact angle measurement", Journal of Colloid and Interface Science, vol. 409 (2013), Apr. 2013, pp. 203-210, Elsevier Inc.
Santini, M. and Guilizzoni, M., "3D X-ray Micro Computed Tomography on Multiphase Drop Interfaces: From Biomimetic to Functional Applications", Journal of Colloid and Interface Science, vol. 1 (2014), Mar. 2014, pp. 14-17, Elsevier B.V.
Feldkamp et al., L.A., "Practical Cone-Beam Algorithm", Journal of Optical Society of America, A/vol. 1, No. 6, Jun. 1984, pp. 612-619.
Homberg et al., "Determining Geometric Grain Structure from X-Ray Micro-Tomograms of Gradated Soil", Schriftenreihe Geotechnik, vol. 21, Jan. 1, 2009, pp. 37-52.
Van Dalen et al., "2D & 3D particle size analysis of mciro-CT images", Bruker Micro-CT User Meeting, Apr. 3, 2012, whole document.

METHOD OF ANALYSING GROUND COFFEE

CROSS-REFERENCE TO RELATED APPLICATION

This application claims the benefit of Italian Patent Application No. IT MI2014A002179 filed Dec. 18, 2014, which is incorporated herein by reference.

FIELD OF THE INVENTION

The present disclosure relates to a method of structural analysis of powder of ground coffee and, in particular, to a method of analysing the grain size of the coffee powder.

BACKGROUND INFORMATION

Roasted coffee grains to be used in a beverage ready for consumption, such as espresso or American coffee, must first be ground, that is, processed in powder form, to better interact with the water passing through the coffee for the extraction of the beverage.

The preparation of coffee, in particular of an espresso coffee, which meets the consumer's taste depends on many factors, among which the grain size of the coffee powder plays an important role. In the traditional preparation of espresso coffee, for example in coffee bars and restaurants, the coffee is purchased in grains and crushing of the grains is made on site by means of a metering device, which carries out the grinding, dispensing ground coffee. The degree of grinding and its control are often left to the experience of the bartender, who makes corrections in case of change of the product in grains and/or of the quality of the dispensed beverage.

In the large-scale retail trade, coffee is often sold in vacuum packages or cans of ground coffee or in the form of capsules or pods ready for use. An analysis of the degree of grinding of the marketed product may be fit or desired for quality control of the product both by the producer and by the purchaser, or to know the characteristics of the product.

To this end, analysis techniques have been developed for the measurement and analysis of the grain size of coffee powder. In general, a characteristic among the most studied is the grain size of the particles of ground coffee. The grain size is typically controlled by determining a distribution curve of the ground coffee as a function of the size of the particles forming the coffee powder, usually indicated with granulometric curve.

A known, fast and inexpensive method is sieving, in which a series of sieves is used with gradually narrower meshes, the sieves being arranged vertically stacked. A predetermined amount of coffee powder is put on the top sieve and all of the sieves in the series are vibrated. The powder collected on each sieve is then weighed. However, the result depends on the amount of powder used, on the duration of the vibratory motion, on the number of sieves used and on environmental factors that modify the aggregation of the particles in the coffee powder (humidity, for example).

The size of the coffee particles can be directly estimated by an optical microscope. A sample of powder is distributed on a slide on which a grid is drawn that indicates the micrometer scale. In addition to problems related to the representativity of the analysed sample, which could be statistically not significant, the evaluation of two particle sizes is only possible with this technique, namely the length and width measured in an optical plane.

A method increasingly used is laser diffractometry, which uses a laser beam at low power in the visible or in the near infrared. The laser beam passes through a sample of coffee powder contained in a cell so as to generate a diffraction pattern which provides information about the particle size distribution. The size range possible with this technique is typically comprised between about 1 and $10^3$ microns. The powder inside the sample can be dispersed in suspension or being in a dry dispersion. The laser diffraction technique is based on a "cumulative" measurement of the sample to obtain the percentage volume of particles having a certain size.

Recently, studies have been published on the microstructural properties of coffee beans (not ground) by using X-ray microtomography. Paola Pittia et al. in "*Evaluation of microstructural properties of coffee beans by synchrotron X-ray microtomography: a methodological approach*", published in the Journal of Food Science, vol. 76 (2011), pages 222-231, describe the use of microtomography based on synchrotron X-ray as a non-destructive imaging technique to study microstructural properties of raw or roasted coffee beans. 2D images were reconstructed with this technique and 3D images of the grains were obtained, which were used to calculate and quantify the porosity of the grains.

P. Frisullo et al. in "*Coffea arabica beans microstructural changes induced by roasting: An X-ray microtomographic investigation*", published in Journal of Food Engineering, vol. 108 (2012), pages 232-237, show 3D images obtained by X-ray microtomography of whole beans of roasted coffee. The authors state that from the 3D image analysis it was possible to derive the size, shape, distribution of the total volume, porosity and density and to quantify the structural alterations of the microstructure caused by the high internal pressure generated during the thermal treatment of roasting.

The interaction between an atomized fluid and a solid surface and in particular of a single droplet deposited on a surface was studied by X-ray computed microtomography (microCT) in "*X-ray computed microtomography for drop shape analysis and contact angle measurement*", published in the Journal of Colloid and Interface Science, Vol. 409 (2013), pages 203-210, by M. Santini et al. The three-dimensional surface of the drop was reconstructed to perform contact angle measurements on the actual cross-sections of the drop-surface pair, with a resolution of about 9 µm.

M. Santini e M. Guilizzoni in "*3D X-ray Micro Computed Tomography on Multiphase Drop Interfaces: From Biomimetic to Functional Applications*" describe three cases of analysis by means of interaction multi-phase microCT, two are microCT of a sessile drop of water on a leaf and the third case is a sessile drop of water on an artificial surface, i.e. a layer of material adapted to the gaseous diffusion (GDL).

SUMMARY OF THE INVENTION

The Applicant has observed that determination of the granulometric curve by laser diffractometry may not allow a measure of "ready to use" coffee powder, for example of the coffee powder contained in a capsule or in a pod. In particular, the Applicant has realized that it would be advantageous to obtain information on the size distribution of particles of coffee contained in a container, for example of plastic or aluminum.

The present disclosure relates to a method for analysing the structure of a sample of ground coffee which comprises:

receiving a plurality of two-dimensional radiographic images of a sample of ground coffee acquired through computed x-ray tomography by detecting x-rays passed through the sample while the sample is in rotation so that each image of the plurality of radiographic images is associated with a respective rotation angle of the sample, which defines the orientation of the sample with respect to a main direction of incidence of the beam;

carrying out a tomographic reconstruction using the plurality of radiographic images to generate a reconstructed volumetric digital image that represents a three-dimensional reconstruction of the sample;

processing the reconstructed volumetric digital image to obtain a processed volumetric digital image to identify a plurality of ground coffee particles of the sample of ground coffee separated from one another, each of the particles being defined by a volumetric surface $A_g$ and by a particle volume $V_g$, and determining at least one dimensional magnitude of each particle of the plurality of ground coffee particles of the processed volumetric digital image.

Preferably, the plurality of particles of ground coffee constitutes the sample of ground coffee.

Some preferred embodiments describe a method for analysing the grain size of the sample of ground coffee wherein determining at least one dimensional magnitude of each particle of the plurality of ground coffee particles contained in the sample comprises determining a volume value $V_g$ of each particle, the method further comprising:

calculating from the volume value $V_g$ of each particle of the plurality of ground coffee particles a respective particle diameter;

calculating a total volume of the plurality of ground coffee particles as a sum of the volume values $V_g$ of the particles, and calculating a percentage volume with respect to the total volume as a function of the particle diameters so as to obtain a granulometric distribution of the ground coffee particles present in the sample.

Preferably, the method further comprises, before calculating a percentage volume with respect to the total volume of the plurality of particles of ground coffee, defining a plurality of granulometric classes, wherein each granulometric class defines a numerical range of values of particle diameters, the numerical ranges being sequential in ascending order and identified by a respective mean value of the diameter and in which the particle size distribution is a function of the mean value of the diameter.

Preferably, the plurality of particles of ground coffee constitutes the sample of ground coffee and the total volume is the total volume of the sample.

In some embodiments, determining at least one dimensional magnitude for each particle of the plurality of ground coffee particles comprises determining a volumetric surface value $A_g$ and a volume value $V_g$ of each particle, the method further comprising:

calculating a total surface of the plurality of ground coffee particles as the sum of the volumetric surface values $A_g$ of each particle of the plurality of particles of ground coffee;

calculating from the volume value $V_g$ of each ground coffee particle a respective particle diameter, and calculating a percentage volumetric surface value with respect to the total volumetric surface of the ground coffee particles as a function of the particle diameters so as to obtain a distribution curve of the surface size of the plurality of ground coffee particles present in the sample.

Preferably, the plurality of particles of ground coffee constitutes the sample of ground coffee and the total surface of the plurality of ground coffee particles is the total volumetric surface of the sample.

Preferably, the method further comprises, before calculating a percentage volumetric surface value, defining a plurality of granulometric classes, wherein each granulometric class defines a numerical range of values of particle diameters, the numerical ranges being sequential in ascending order and identified by a respective average value of the diameter and in which the particle size distribution is a function of the average value of the diameter.

In some embodiments, determining at least one dimensional magnitude for each ground coffee particle of the plurality comprises determining a volume value $V_g$ of each particle of the plurality of ground coffee particles, the method further comprising:

calculating from the volume value $V_g$ of each ground coffee particle a respective particle diameter value, defining a plurality of granulometric classes, wherein each granulometric class defines a numerical range of particle diameter values, the numerical ranges being sequential in ascending order and identified by a respective average diameter value, and counting the number of particles of the plurality of ground coffee particles for each granulometric class so as to obtain a number density distribution of the plurality of ground coffee particles present in the sample.

In an embodiment, the particle diameter is the equivalent diameter.

In a further embodiment, the particle diameter is the Sauter diameter defined as $d_{32} = 6 V_g/A_g$.

Preferably, processing the reconstructed volumetric digital image to identify a plurality of coffee particles comprises:

extracting a plurality of reconstructed slice digital images as axial projections of the reconstructed volumetric digital image on planes parallel one to another and perpendicular to a vertical axis of the three-dimensional reconstruction of the sample;

processing each reconstructed slice digital image of the plurality of reconstructed slice digital images so as to obtain a respective plurality of processed slice digital images, and juxtaposing the processed slice digital images one on the other on parallel planes along the vertical axis so as to generate the processed volumetric digital image and to define the volumetric surface $A_g$ and the volume $V_g$ of each particle of the plurality of ground coffee particles.

In an embodiment, processing each reconstructed slice digital image of the plurality of reconstructed slice digital images comprises:

(i) transforming a first reconstructed slice image of the plurality of reconstructed slice digital images into a first binary image through a digital binarization filter, the first binary image highlighting coffee particles with respect to a homogeneous background;

(ii) transforming the first binary image into a second binary image in which the particles displayed in the image are separated from one another and are defined by contour lines, and (iii) repeating the steps (i) and (ii) for the remaining reconstructed slice images of the plurality of reconstructed slice digital images to generate a respective plurality of processed slice digital images.

Preferably, the three-dimensional reconstruction of the sample is rendered in voxels that define the three-dimensional resolution of the reconstructed sample and wherein the plurality of processed slice digital images are arranged at an axial distance from one another, which is equal to the spatial resolution of the two-dimensional radiographic images, generating a plurality of interconnected voxel groups, each voxel group representing a single coffee powder particle.

Preferably, the volume $V_g$ of each coffee particle of the plurality of particles is determined by adding together the voxels constituting a voxel group that represents the particle.

In an embodiment, step (ii) is carried out by applying a watershed digital transformation filter.

In some embodiments, the sample is a capsule or a pod of ground coffee.

Preferably, the method further comprises, prior to receiving a plurality of two-dimensional radiographic images:
  irradiating the sample of ground coffee with a beam of X-rays emitted by a source of X-rays, and
  detecting the X-ray beam that passes through the sample while the sample is rotated by means of a detector device, wherein the detector device is configured to convert X-rays into digitalized signals and to generate radiographic two-dimensional digital images.

Preferably, in the step of receiving the plurality of radiographic images, the sample is in rotation around an axis substantially perpendicular to the main direction of incidence of the beam on the sample.

The two-dimensional radiographic images are digital images or images digitized prior to the step of performing a tomographic reconstruction from the plurality of two-dimensional radiographic images.

Preferably, the X-ray source is a microfocus source.

BRIEF DESCRIPTION OF THE DRAWINGS

Further features and advantages of the invention will be apparent from the following detailed description made with reference to some embodiments given by way of non-limiting examples and to the accompanying figures, in which:

FIG. 8b is a graph that shows the distribution of the percentage volumetric surface of the single particles as a function of the equivalent diameter for blends A, B, C and D of FIG. 8a.

FIG. 9 is an exemplary graph that shows the percentage volume of the particles constituting the coffee powder (black solid circles) as a function of the Sauter diameter, namely a granulometric curve for blend D in FIG. 8a.

DETAILED DESCRIPTION

Figure 1:
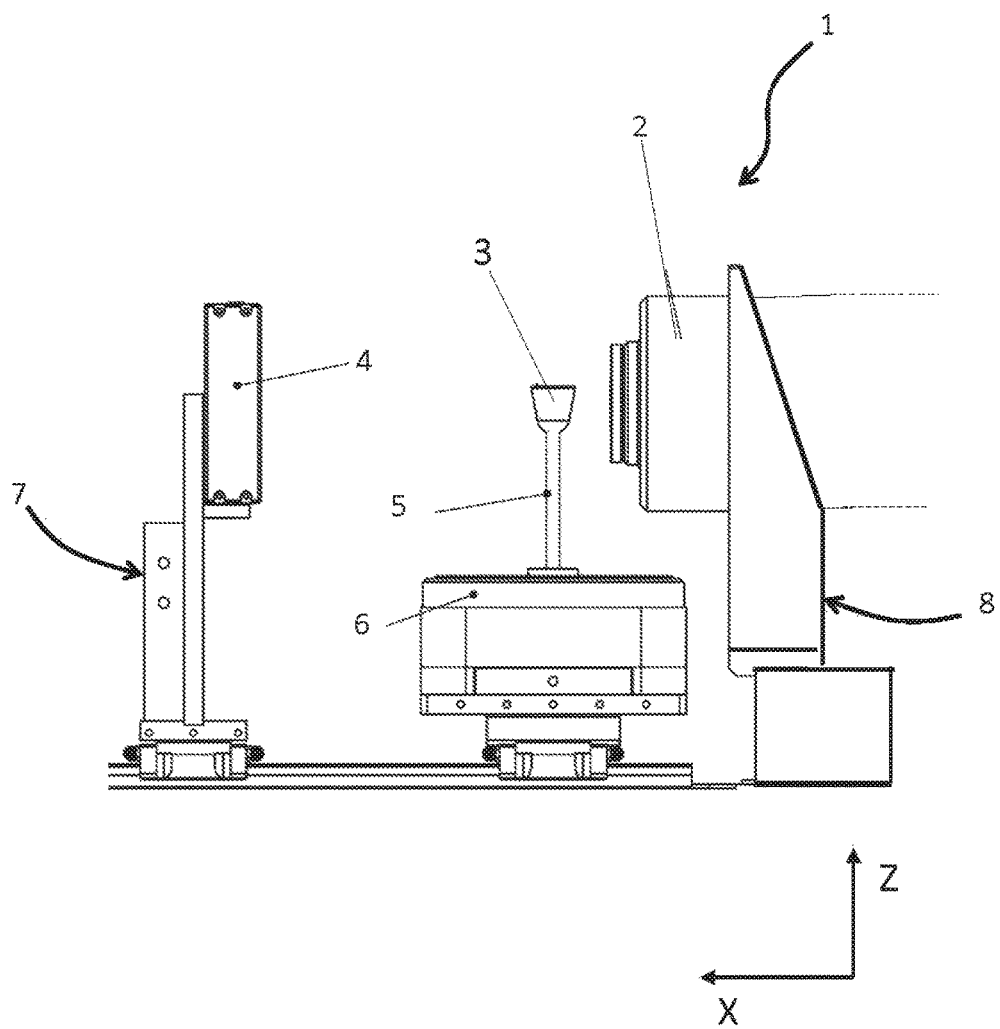
FIG. 1 schematically shows a measurement apparatus suitable for performing the method according to the present disclosure.

FIG. 1 shows a measurement apparatus suitable for performing the method according to the present invention. An X-ray computed tomography apparatus 1 comprises an X-ray source 2 configured to emit an X-ray beam that can be emitted with a focusing spot equal to about 1 µm or less. For example, the source is an open tube source with microfocus operating with voltages up to 160 kVp and currents up to 200 µA. In some preferred embodiments, the focusing spot is selected to be equal to 1 µm. However, it is possible to use a focal spot of smaller dimensions, for example when the degree of compaction of the ground coffee is higher, or use greater emission powers when the panel of ground coffee is contained in radio opaque containers, such as for example metal or plastic containers, such as coffee filters.

Preferably, the X-ray source is a microfocus source.

The X-ray beam is acquired by a detector device 4 configured to detect two-dimensional radiographic images. Preferably, the detector device comprises a photodetector in the visible optically coupled to a scintillator for the wavelength conversion of X-rays into light in the visible. The scintillator is configured to convert the X-ray beam that has passed through the sample in an optical signal which impinges on the photodetector. In some embodiments, the photodetector is a CCD sensor or a CMOS sensor. For example, the resolution of the photodetector is 50 µm.

In the usual ways, the detector device and the source (shown only partially in FIG. 1) are mounted on respective support bases 7 and 8 to allow or facilitate the optical alignment between the elements of the apparatus. Without loss of generality of the present disclosure, the beam emitted from an open tube source is conical in shape and a main axis of the beam emitted by the source can be defined, the axis in the apparatus in FIG. 1 coinciding with a main direction of incidence of the beam on the sample, indicated with axis X in the figure.

A sample 3 is positioned between source 2 and the detector device 4 in such a way as to be traversed by the beam emitted by the source. In some embodiments, the sample is a capsule or a pod of pre-dosed ground coffee. Sample 3 is mounted on a sample holder 5, in turn mounted on a support base 6. The support base 6 can rotate around a central rotation axis, indicated with axis Z in FIG. 1, and it carries the sample holder with it in such a way that, during the measurements, different angular positions of the sample are exposed to the X-ray beam emitted by the source. Preferably, the rotation axis is perpendicular to the main direction of incidence of the X-ray beam on the sample.

Preferably, the support base 6 is a table rotatable on an air cushion, actuated by a contactless magnetic field motor. Such a rotation mechanism allows maintaining the rotation axis constant during the tomographic acquisition with oscillations due to vibrations of less than 500 nm, then generally negligible compared to the range of spatial resolutions used.

The rotation of the sample, the acquisition of the detector device and the source are controlled by a processor (not shown in FIG. 1) in such a way that it is possible to program the angles of rotation of the sample (e.g. the angular steps in which to subdivide a rotation of)360°), the times of acquisition, the number of images acquired at a certain angle of rotation and the optical parameters of the beam emitted by the source.

During tomographic measurements, the sample is placed in rotation and the detector device detects a series of two-dimensional (2D) radiographic images generated by the attenuation of X-rays through the sample in such a way that each acquired radiographic image corresponds to an angular position of the sample defined by an angle of rotation.

In known ways, the quality of a 2D radiographic image acquired at an angular position depends also on the integration time. In addition, in order to decrease the noise in the data acquired, it may be desirable to acquire a series of images at a certain angle of rotation, then calculating an image obtained from the mean value of the series of images. In the present context, when referring to a 2D X-ray image associated with a rotation angle, it may also be understood that an image is the mean value of a series of acquisitions. In some embodiments, a single 2D radiographic image is acquired for each rotation angle, and the integration time is suitably selected so as to obtain the desired quality.

The method comprises receiving a plurality of 2D radiographic images from the detector device acquired while the sample is in rotation about an axis transverse to the main direction of incidence of the beam on the sample, in such a way that each radiographic image of the plurality is associated with a respective rotation angle θ of the object. The rotation angle describes the orientation of the object relative to the direction of incidence of the X-ray beam and hence the object angular portion of exposure to the beam. Preferably, the measurements are acquired during a complete rotation of the sample, i.e. 360°.

The 2D X-ray images, detected by the detector device, are preferably acquired as digital images by a processor (not shown in FIG. 1) logically connected to the detector device so as to receive the output signals. The 2D X-ray images, digital or digitized in case they are acquired by the processor in analog form, are recorded as two-dimensional arrays of pixels, whose number of pixels and the size of a single pixel mainly depend on the spatial resolution of the detector device.

Subsequently, the method comprises processing the 2D radiographic images by performing a tomographic reconstruction to generate a three-dimensional image of the object structure, e.g. the panel of ground coffee, from the plurality of 2D radiographic images. In the preferred embodiments, the tomographic reconstruction of the sample from the radiographic image is a volumetric reconstruction of the object from 2D radiographic images, known per se, which can be performed by using reconstruction algorithms, such as filtered back projection algorithms. For example, the tomographic reconstruction uses the filtered back-projection algorithm of Feldkamp-Davis-Kress (FDK) for diverging conical beams, described in J. Opt. Soc. Am. Al (1984), pages 612-619. Reconstruction algorithms can be implemented in commercial software. The volumetric reconstruction is rendered in volume elements (voxels, i.e. volumetric pixels) that define the three-dimensional resolution of the reconstructed object. The 3D volume is displayed graphically, for example on a computer screen, and as is generally known, from the reconstructed 3D volume it is possible to derive one or more 2D projections in a plane which passes through the volume, and in particular one or more 2D cross sections (hereinafter described with reconstructed slice images), or to extract a 3D model of the surface of the object. In manners known per se, the size of the voxel in pixel unit is converted into a physical dimension by calibration of the computed tomography apparatus.

Without loss of generality of the present invention, the following description related to FIGS. 3-7 relates to preferred forms of digital volumetric reconstruction of the sample, in which the three-dimensional (3D) volume is obtained by the recombination of reconstructed 2D slice images processed as described below.

Figure 2:
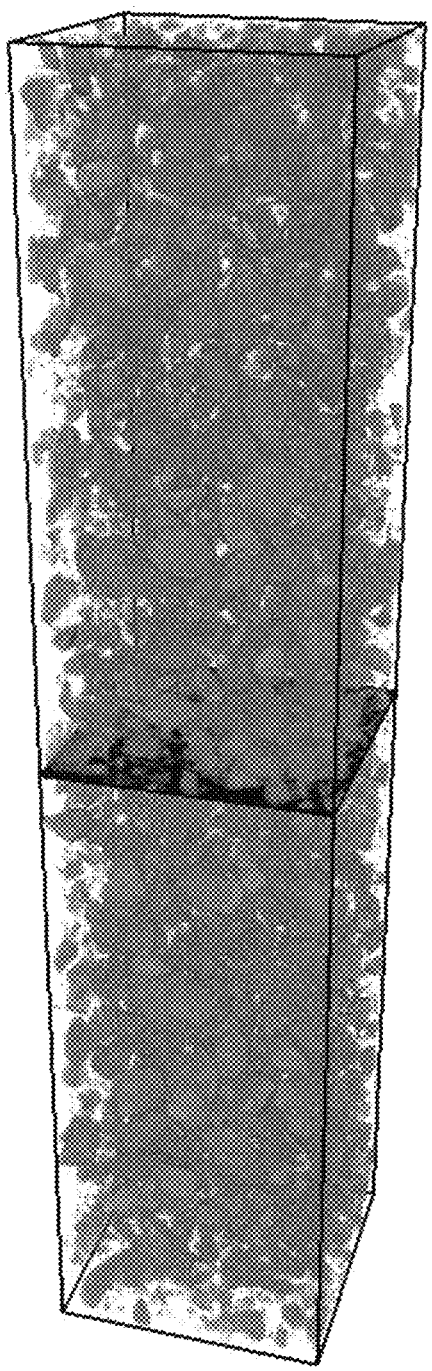
FIG. 2 shows an example of three-dimensional reconstruction for a parallelepiped sub-volume virtually extracted from a three-dimensional reconstruction of an uncompressed sample of ground coffee powder analysed with the X-ray computed tomographic technique.

FIG. 2 shows a digital image of the three-dimensional reconstruction of a parallelepiped sub-volume, which has been virtually extracted in a central portion of the 3D reconstruction of an uncompressed sample of ground coffee powder, measured by the computed X-ray tomographic technique. In the reconstruction, individual particles making up the coffee powder are visible.

Figure 3:
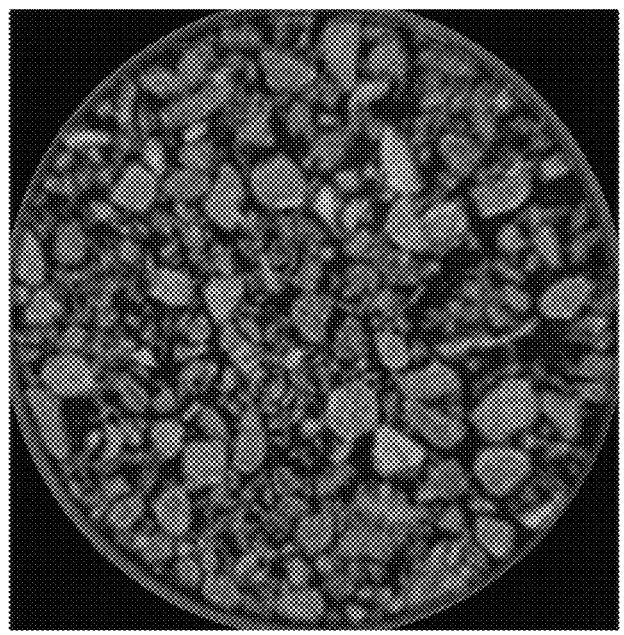
FIG. 3 shows an example of a reconstructed digital image of a 2D axial slice of the volumetric reconstruction of a sample of ground coffee contained in a cylindrical container and analysed with the X-ray computed tomographic technique.

FIG. 3 shows a reconstructed 2D slice image of the volumetric reconstruction of a sample of ground coffee contained in a container of cylindrical shape, whose edge of circular shape is visible in the image. The shown cross-section is an axial slice in a plane perpendicular to the height of the cylinder, i.e. thickness of the sample, more generally perpendicular to the vertical axis of the sample. The particles that constitute the coffee powder, displayed in gray color of different shades, are visually distinguishable from air, indicated with a black color.

In order to determine the size of the individual particles of ground coffee of the reconstructed volume of the sample, the method, in its preferred embodiments, proceeds with an automatic procedure of image processing so as to define and highlight the individual particles.

Figure 4:
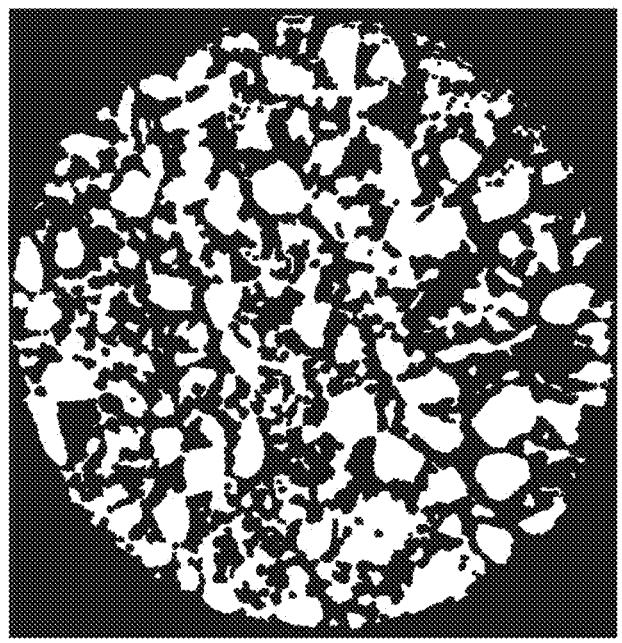
FIG. 4 is a binary digital image obtained from the image in FIG. 3, in which the isosurface of the particles is displayed with white color on a black background.

Preferably, the automatic procedure of image processing comprises:

a) receiving as input data a plurality of 2D reconstructed images related to cross sections in planes parallel to each other. Preferably, the 2D reconstructed images are axial slices and the plurality of 2D reconstructed images, if juxtaposed along an axis perpendicular to the parallel planes and arranged at an axial distance equal to a pixel, form the volumetric reconstruction of the ground coffee;

b) transforming a 2D reconstructed image of the plurality of 2D reconstructed images and relative to a cross section into a binary image by using a digital binarization filter. The digital binarization filter is typically realized by means of mathematical algorithms suitable for image processing. In the binary digital image, the particles are represented with a constant value of color and highlighted with a high contrast with respect to a homogeneous background. FIG. 4 is a binary digital image obtained from the transformation of the image in FIG. 3, in which the isosurface of the particles is displayed with white color on a black background.

FIG. 4 shows that many particles have points of contact with adjacent particles. In order to assess the size of the individual particles, it is preferable to define and highlight, in the binary image, each single particle by isolating it from the other particles.

Subsequent to the binarization of the 2D reconstructed slice image, the automatic procedure of image processing comprises: c) transforming the binarized image by separating the particles from one another by the application of a digital image processing filter. In an embodiment, the digital filter is a watershed transformation filter.

Figure 5:
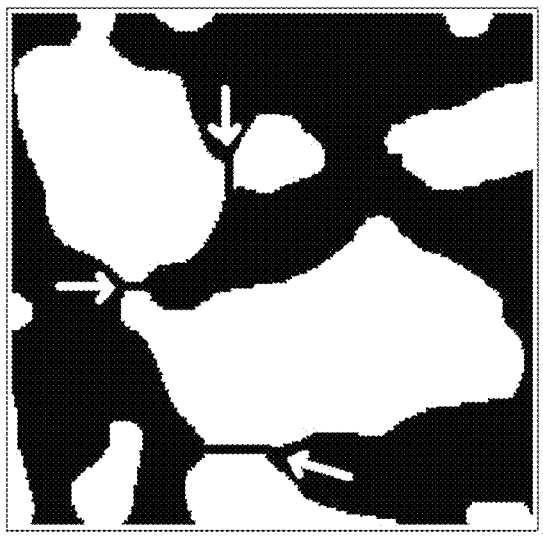
FIG. 5 is an enlargement of a portion of FIG. 4, in which the separation lines (in black) between adjacent particles are indicated with white arrows, the separation lines having been calculated by a watershed transformation algorithm applied to the image in FIG. 4.
Figure 6:
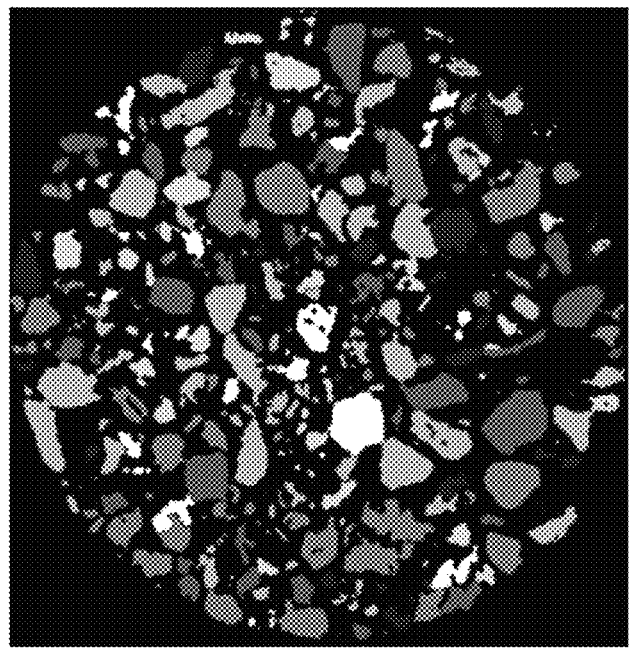
FIG. 6 is the image resulting from the watershed transformation of the image in FIG. 4.

FIG. 5 is an enlargement of a portion of the image in FIG. 4, in which the separation lines (in black) between adjacent particles are indicated with white arrows, separation lines being calculated by the watershed algorithm, whereas FIG. 6 shows the image resulting from the watershed transformation of the image in FIG. 4. The watershed transformation, starting from a binary image, generates a binary image. However, in order to more visually differentiate the particles in the image, the particles in FIG. 6 are shown with different shades of gray, attributed in the shade using a geometric magnitude of the particles themselves.

The image processing procedure described above in steps b) and c) is repeated for each of the images of the plurality of reconstructed axial slice images. The axial slices of the reconstruction are spaced apart from one another by a magnitude equivalent to the resolution of the reconstruction, equal to the dimension of the side of the pixels in the 2D reconstructed images. Therefore, by juxtaposing the reconstructed axial slice images thus processed one on top of the other along the axial direction perpendicular to the slice planes, it is possible to identify all the particles of the coffee powder in the sample, generating interconnected groups of voxels, each group of voxel representing a single particle of coffee powder. Each particle of coffee is characterized by a respective numerical value equivalent to the 3D volume determined by the number of voxels that make it up. Every single voxel is uniquely determined in the 3D reconstruction allowing measurement of the volume of each particle as the sum of the number of the voxels that make it up. The voxel thus reconstructed is an isotropic cubic-shaped element.

The volume, $V_g$, of each particle and preferably its 3D surface, $A_g$, are calculated, respectively, by the summation of all the voxels constituting the group of voxels, and of all the non-adjacent surfaces of the voxel themselves. After determining the size of each particle, the granulometric curve of the coffee powder contained in the sample is determined.

Figure 7:
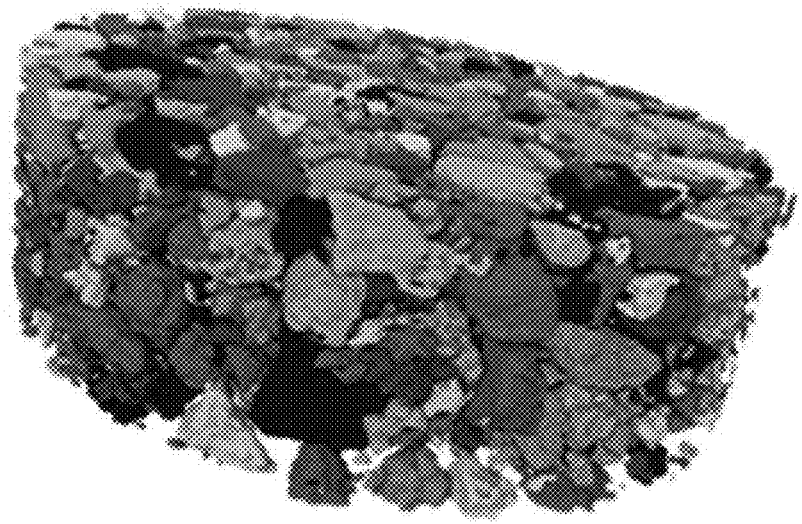
FIG. 7 is a digital image of the three-dimensional volumetric reconstruction of a panel of coffee resulting from the processing method according to an embodiment of the present invention.

FIG. 7 is a three-dimensional image of a panel of coffee, resulting from the image processing method described above, in which the constituent particles of the coffee powder of the reconstructed slice images were processed, defining the respective outer surface thereof. In the image, each particle of coffee is distinguishable from the others. The container is not visible in the image because it has been virtually removed by applying image processing digital filters known per se. The grayscale display is to better visually distinguish the particles from one another.

According to an embodiment, from the volume of a particle of coffee, $V_g$, the equivalent diameter, $d_e$, is calculated assuming that the particle is a sphere, $$d_e = \sqrt[3]{\frac{6V_g}{\pi}}.\qquad(1)$$

In a preferred embodiment, the Sauter diameter, $d_{32}$, is calculated for each particle, which is defined as the ratio between the volume of each individual granule and its surface, $$d_{32} = 6V_g/A_g \qquad(2)$$

Once the Sauter diameter (or equivalent diameter) is known, the volumetric percentage of particles within the volume of the sample, which have a certain diameter is calculated. In practice, values $d_{32}$ of the particles are divided into classes, generally indicated with BIN, each class defining a range of values, of which the mean value is indicated in the graph. The range of values that identifies a granulometric class can be the same for all classes, e.g. 10 µm. The volume sum of the volumes having diameter values comprised in the class is calculated for each class and the volume percentage with respect to the total volume of the coffee particles for said granulometric class is calculated.

The possibility offered by the present method of determining the surface of each single granule of ground coffee allows studying the surface distribution of the granules according to the diameter of the same in a sample.

Figure 8A:
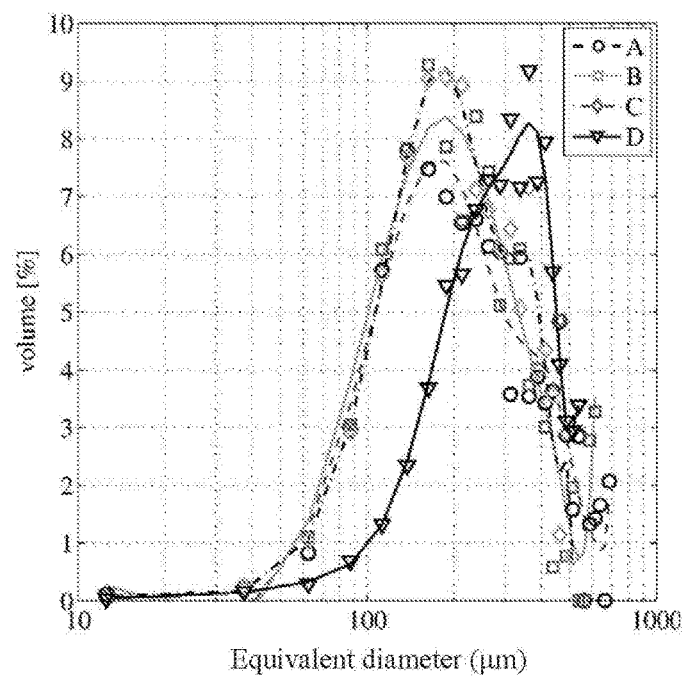
FIG. 8a shows four exemplary curves, each representing the percentage volume of the particles constituting the coffee powder as a function of the equivalent diameter, or granulometric curve, for four respective different coffee blends (curves A, B, C and D).
Figure 8B:
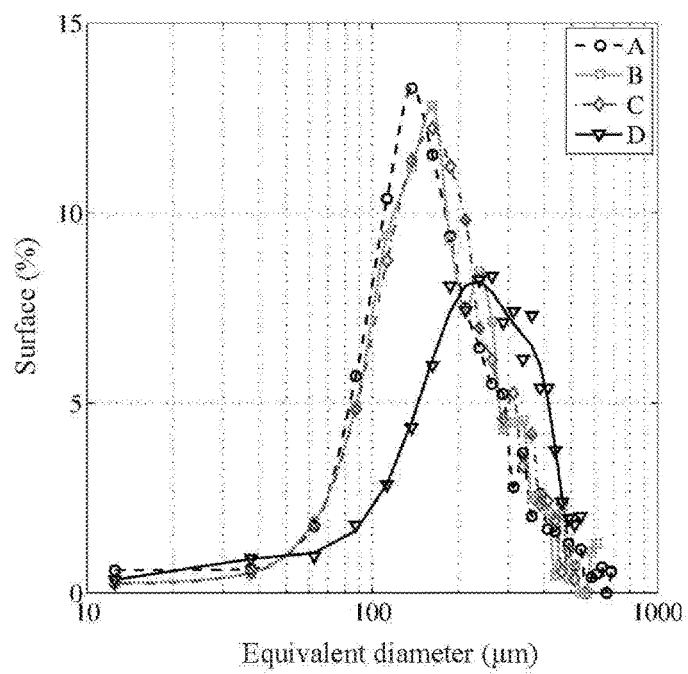

FIG. 8a shows a granulometric curve as a function of the equivalent diameter, calculated using Eq. (1), for three different coffee blends (curves A, B and C) having an apparent similar degree of grinding and a fourth coffee blend with different degree of grinding (curve D). The peak of the curve is centered at a diameter of about 200 µm for blends A, B and C, while the peak is centered at a diameter of approximately 480 µm for blend D. FIG. 8b is a graph that shows the surface distribution of the individual particles, represented by a percentage surface value of the particles (volumetric surface) with respect to the total volumetric surface of all the particles, as a function of the equivalent diameter for blends A, B, C and D of FIG. 8a. The curves in FIGS. 8a and 8b were calculated with BIN of 25 µm.

Figure 9:
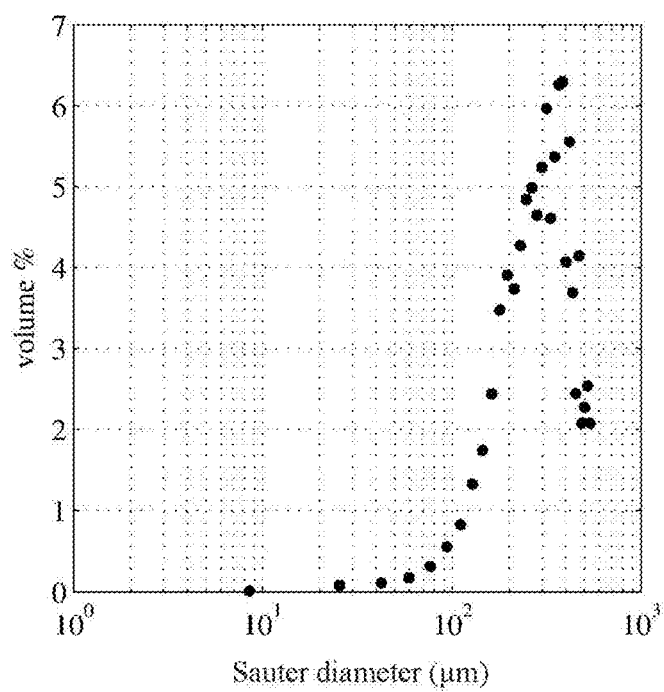

FIG. 9 is an exemplary graph which shows the percentage volume of the particles constituting the coffee powder (black solid circles) as a function of the Sauter diameter, i.e. the granulometric curve for a sample of ground coffee for a blend corresponding to that represented with curve D in FIG. 8a and BIN equal to 17 µm.

Figure 10:
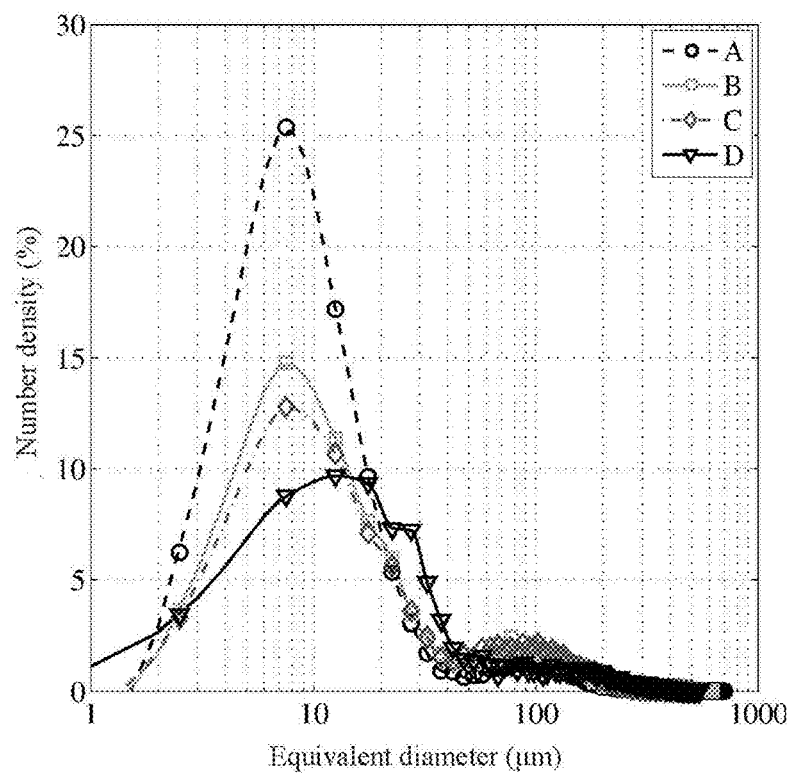
FIG. 10 is a graph that shows the percentage number density as a function of the equivalent diameter for the blends analysed in the graphs in FIGS. 8a and 8b.

FIG. 10 is a graph that shows the distribution of the number of granules having a given size, counting how many granules are present in a given class, each class being represented by an average value of particle diameter. In particular, the percentage number density is shown as a function of the equivalent diameter for the blends analysed in the graphs in FIGS. 8a and 8b. The graph in FIG. 10 shows that, although the larger granules are those which contribute the most to the total volume, the smaller granules are present in greater number with a prevalence of granules having an equivalent diameter of about 8 µm. It is also noted that blend A, which shows a granulometric curve similar to those of blends B and C (FIG. 8a), has a number density distribution significantly different from those of blends B and C, due to a greater presence of "dust", i.e. very small particles.

By the method according to the present invention it is possible to analyse coffee powder in capsules or pods ready for use.

Figure 11:
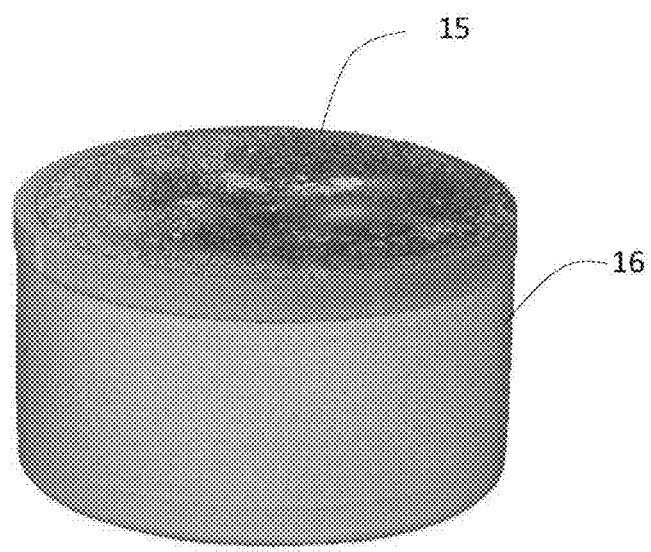
FIG. 11 is a digital image of the three-dimensional reconstruction of a capsule of ground coffee ready for use.

FIG. 11 is a digital image of the three-dimensional reconstruction of a capsule of ground coffee ready for use, measured by the computed tomographic technique according to the present invention. In the reconstruction, the outer container 16, a polymer capsule having a cylindrical shape, and the coffee powder 15 contained therein can be seen. The capsule had a diameter of about 30 mm. In order to analyse a capsule of such a size, a suitable detector device of an appropriate size was selected, positioned at a distance such as to maintain the resolution to values compatible with the minimum detectable size of a particle of ground coffee. In the example in FIG. 11, the detector device comprised a CMOS with 4096 pixels per side and linear pixel size of 100 μm, placed at a distance from the source, along direction X (see FIG. 1), equal to 410 mm. By way of example, a distance of 50 mm between the detector device and the source allows a theoretical magnification of 13 times and thus a resolution of 7.3 μm side equivalent of a voxel in the reconstructed volume. A plurality of two-dimensional radiographic images were acquired in planes parallel to the height of the capsule while the sample rotated about an axis parallel to the height of the capsule. The tomographic reconstruction algorithm used for the volumetric reconstruction of the coffee sample was an FDK algorithm. A plurality of axial slices (reconstructed slice images) were extracted from the volumetric reconstruction.

Figure 12:
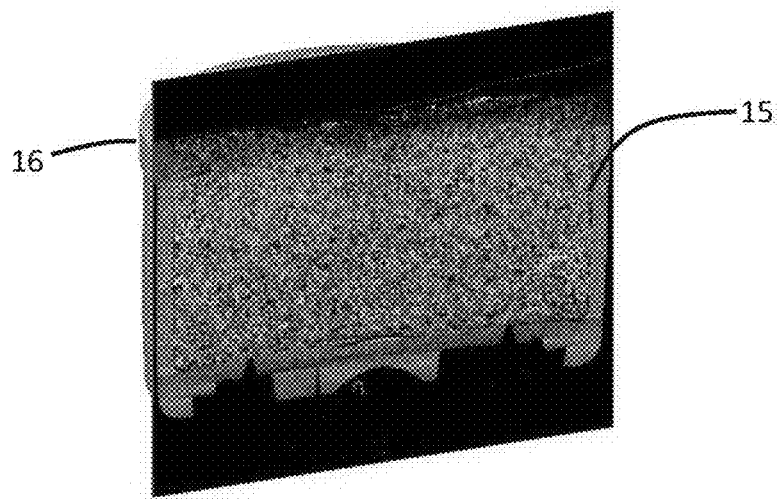
FIG. 12 is the image of a vertical cross-section of the reconstructed volume in FIG. 11.

FIG. 12 shows a cross section along a plane parallel to the height of the capsule of the reconstructed volume in FIG. 11.

Figure 13:
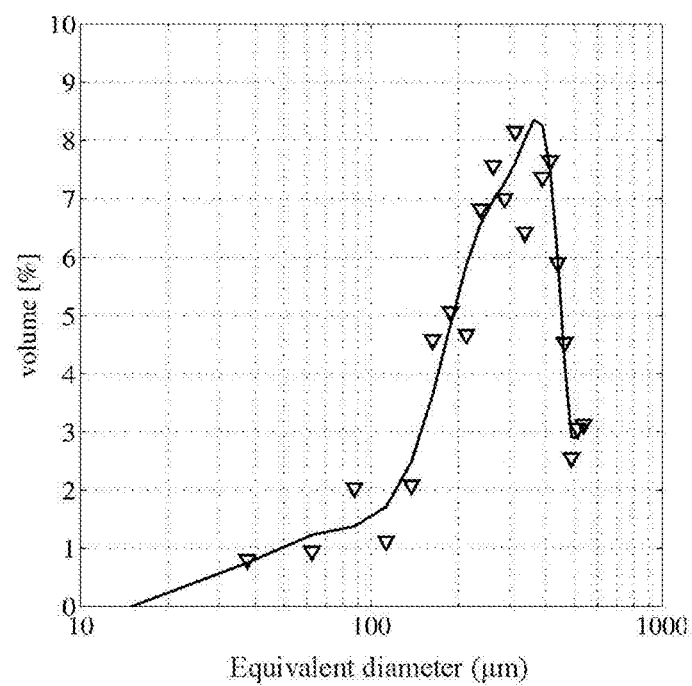
FIG. 13 shows a granulometric curve as a function of the equivalent diameter for the sample of ground coffee in FIGS. 11 and 12.

FIG. 13 shows the granulometric curve as a function of the equivalent diameter for the sample of ground coffee in FIGS. 11 and 12. The image processing of the volumetric reconstruction was obtained by a procedure similar to that described with reference to FIGS. 3-7.

What is claimed is:

1. A method for analysing the structure of ground coffee contained in a capsule or in a pod, the method comprising:
   receiving a plurality of two-dimensional radiographic images of a sample of ground coffee acquired through computed X-ray tomography by detecting X-rays passed through the sample while the sample is in rotation so that each image of the plurality of radiographic images is associated with a respective rotation angle of the sample, which defines the orientation of the sample with respect to a main direction of incidence of the beam;
   carrying out a tomographic reconstruction using the plurality of radiographic images to generate a reconstructed volumetric digital image that represents a three-dimensional reconstruction of the sample;
   processing the reconstructed volumetric digital image to obtain a processed volumetric digital image to identify a plurality of coffee particles of the sample of ground coffee separated from one another, each of the particles being defined by a volumetric surface $A_g$ and by a particle volume $V_g$, and
   determining at least one dimensional magnitude of each particle of the plurality of ground coffee particles by:
      determining a volumetric surface value $A_g$ and a volume value $V_g$ of each particle;
      calculating a total volumetric surface of the plurality of ground coffee particles as sum of the volumetric surface values $A_g$ of each particle of the plurality;
      calculating from the volume value $V_g$ of each ground coffee particle a respective particle diameter; and
      calculating a percentage volumetric surface value with respect to the total volumetric surface of the ground coffee particles as a function of the particle diameters so as to obtain a distribution curve of the surface size of the ground coffee particles present in the capsule or pod.

2. The method according to claim 1, wherein the diameter is an equivalent diameter.

3. The method according to claim 1, wherein the diameter is a Sauter diameter defined as $d_{32} = 6 V_g/A_g$.

4. The method according to claim 1, wherein processing the reconstructed volume digital image to identify a plurality of coffee particles comprises:
   extracting a plurality of reconstructed slice digital images as axial projections of the reconstructed volume digital image on planes parallel one to another and perpendicular to a vertical axis of the reconstructed volume;
   processing each reconstructed slice digital image of the plurality of reconstructed slice digital images so as to obtain a respective plurality of processed slice digital images, and
   juxtaposing the processed slice digital images one on the other on parallel planes along the vertical axis so as to generate the processed volumetric digital image of the sample and to define the volumetric surface $A_g$ and the volume $V_g$ of each particle of the plurality of ground coffee particles.

5. The method according to claim 4, wherein processing each reconstructed slice digital image of the plurality of reconstructed slice digital images comprises:
   (i) transforming a first reconstructed slice image of the plurality of reconstructed slice digital images into a first binary image through a digital binarization filter, the first binary image highlighting coffee particles with respect to a homogeneous background;
   (ii) transforming the first binary image into a second binary image in which the particles displayed in the image are separated from one another and are defined by contour lines, and
   (iii) repeating the steps (i) and (ii) for the remaining reconstructed slice images of the plurality of reconstructed slice digital images to generate a respective plurality of processed slice digital images.

6. The method according to claim 5, wherein step (ii) is carried out by applying a watershed digital transformation filter.

7. The method according to claim 4, wherein the three-dimensional reconstruction of the sample is rendered in voxels that define the three-dimensional resolution of the reconstructed sample and wherein the plurality of processed slice digital images are arranged at an axial distance one from another equal to the spatial resolution of the two-dimensional radiographic images, generating a plurality of interconnected voxel groups, each voxel group representing a single ground coffee particle.

8. The method according to claim 4, wherein the three-dimensional reconstruction of the sample is rendered in voxels that define the three-dimensional resolution of the reconstructed sample and wherein the plurality of processed slice digital images are arranged at an axial distance one from another equal to the spatial resolution of the two-dimensional radiographic images, generating a plurality of interconnected voxel groups, each voxel group representing a single ground coffee particle and wherein the volume $V_g$ of each coffee particle of the plurality of particles is determined by adding together the voxels constituting a voxel group that represents the particle.

9. A method for analysing the structure of ground coffee contained in a capsule or in a pod, the method comprising:

receiving a plurality of two-dimensional radiographic images of a sample of ground coffee acquired through computed X-ray tomography by detecting X-rays passed through the sample while the sample is in rotation so that each image of the plurality of radiographic images is associated with a respective rotation angle of the sample, which defines the orientation of the sample with respect to a main direction of incidence of the beam;

carrying out a tomographic reconstruction using the plurality of radiographic images to generate a reconstructed volumetric digital image that represents a three-dimensional reconstruction of the sample;

processing the reconstructed volumetric digital image to obtain a processed volumetric digital image to identify a plurality of coffee particles of the sample of ground coffee separated from one another, each of the particles being defined by a volumetric surface $A_g$ and by a particle volume $V_g$, and determining at least one dimensional magnitude of each particle of the plurality of ground coffee particles, wherein determining at least one dimensional magnitude for each ground coffee particle of the plurality comprises determining a volume value $V_g$ of each particle of the plurality of ground coffee particles, the method also comprising:

calculating from the volume value $V_g$ of each ground coffee particle a respective particle diameter value, defining a plurality of granulometric classes, wherein each granulometric class defines a numerical range of particle diameter values, the numerical ranges being sequential in ascending order and identified by a respective average diameter value, and counting the number of particles of the plurality of ground coffee particles for each granulometric class so as to obtain a number density distribution of the plurality of ground coffee particles present in the capsule or pod.

10. The method according to claim 9, wherein the diameter is the equivalent diameter.

11. The method according to claim 10, wherein the method also comprises determining the surface $A_g$ of each ground coffee particle and the diameter is a Sauter diameter defined as $d_{32}=6\ V_g/A_g$.

12. A method for analysing the grain size of ground coffee contained in a capsule or in a pod, the method comprising:

receiving a plurality of two-dimensional radiographic images of a sample of ground coffee acquired through computed X-ray tomography by detecting X-rays passed through the sample while the sample is in rotation so that each image of the plurality of radiographic images is associated with a respective rotation angle of the sample, which defines the orientation of the sample with respect to a main direction of incidence of the beam;

carrying out a tomographic reconstruction using the plurality of radiographic images to generate a reconstructed volumetric digital image that represents a three-dimensional reconstruction of the sample;

processing the reconstructed volumetric digital image to obtain a processed volumetric digital image to identify a plurality of coffee particles of the sample of ground coffee separated from one another, each of the particles being defined by a volumetric surface $A_g$ and by a particle volume $V_g$;

determining at least one dimensional magnitude of each particle of the plurality of ground coffee particles, wherein determining comprises determining a volume value $V_g$ of each particle;

calculating from the volume value $V_g$ of each ground coffee particle a respective particle diameter;

calculating a total volume of the plurality of ground coffee particles as a sum of the volume values $V_g$ of the particles, and calculating a percentage volume with respect to the total volume as a function of the particle diameters so as to obtain a granulometric distribution of the ground coffee particles present in the capsule or pod.

13. The method according to claim 12, wherein the diameter is the equivalent diameter.

14. The method according to claim 12, wherein the method also comprises determining the surface $A_g$ of each ground coffee particle and the diameter is the Sauter diameter defined as $d_{32}=6\ V_g/A_g$.

* * * * *